United States Patent
Elist et al.

(10) Patent No.: US 8,652,107 B1
(45) Date of Patent: Feb. 18, 2014

(54) ARTICLE FOR SECURING A CATHETER

(71) Applicant: James J. Elist, a Medical Corporation, Beverly Hills, CA (US)

(72) Inventors: James Elist, Beverly Hills, CA (US); Gene Scott, Irvine, CA (US)

(*) Notice: Subject to any disclaimer, the term of this patent is extended or adjusted under 35 U.S.C. 154(b) by 0 days.

(21) Appl. No.: 13/754,701

(22) Filed: Jan. 30, 2013

(51) Int. Cl.
*A61M 5/32* (2006.01)

(52) U.S. Cl.
USPC ............ 604/180; 604/178; 604/250

(58) Field of Classification Search
USPC ............ 604/174, 175, 178, 180, 250
See application file for complete search history.

(56) References Cited

U.S. PATENT DOCUMENTS

| | | | |
|---|---|---|---|
| 4,645,492 A * | 2/1987 | Weeks | 604/174 |
| 2009/0137944 A1* | 5/2009 | Haarala et al. | 604/44 |
| 2012/0004616 A1* | 1/2012 | Mitra | 604/175 |
| 2013/0075429 A1* | 3/2013 | Houser | 222/153.11 |

* cited by examiner

*Primary Examiner* — Emily Schmidt
(74) *Attorney, Agent, or Firm* — Patent Law & Venture Group; Gene Scott

(57) ABSTRACT

An article prevents a drainage tube or catheter from being inadvertently moved, removed, or constricted. The article generally includes (i) a hollow conduit having a medial bend formed with an angle of between 45 and 135 degrees, and further having a lateral opening in a wall of the conduit, the opening exposing an interior space within the conduit, the wall having a means for securing a retainer in a selected position relative to the opening, (ii) a catheter positioned coaxially within the conduit, the catheter having a catheter wall, and (iii) the retainer removably secured within the opening wherein a tooth of the retainer penetratingly positioned within the catheter wall.

14 Claims, 4 Drawing Sheets

ARTICLE FOR SECURING A CATHETER

BACKGROUND

This disclosure relates to the field of medical devices and more particularly to a medical device for securing a catheter which may be partially engaged within a body (e.g., human body).

A catheter is a tube often inserted in the body to treat diseases or perform a surgical or other medical procedure. By modifying the material or adjusting the way catheters are manufactured, it is possible to adapt catheters for cardiovascular, urological, gastrointestinal, neurovascular, ophthalmic, and other applications.

Catheters allow drainage, administration of fluids or gases, access by surgical instruments, and also are able to perform a wide variety of other tasks depending on the application. In most uses, a catheter is a thin, flexible tube ("soft" catheter), though catheters are available in varying degrees of stiffness. When body fluids must be drained, a portion of a catheter may be secured within the body temporarily or also permanently.

In use, catheters may be accidently or inadvertently removed from a body or undesirably moved within the body. Furthermore, a catheter may become accidentally or inadvertently pinched, kinked, or otherwise constricted, e.g., by clothing or body movements.

Potentially life-threatening complications can result from inadvertent removal or repositioning of a catheter. Thus, it is desirable to secure an exterior portion of a catheter and to prevent it from being constricted.

In some cases, it may be desirable to conduct an exterior portion of a catheter along the surface of the body from which it extends in order to avoid the problems described above. The prior art fails to teach a means for turning a catheter at a right angle immediately after immerging normally from a body surface. The prior art also fails to disclose how such a redirecting of a catheter may be accomplished without pinching it or otherwise constricting its flow. The prior art also fails to disclose how such a turning and non-obstructing of such a catheter might be accomplished while also directing the exterior portion of the catheter in a selected direction. The prior art also fails to disclose how to hold a catheter in place while accomplishing the foregoing. Finally, prior art catheter holders tend to be complex, expensive and cumbersome to use. The device of this disclosure overcomes the above problems and has further advantages as described in the following detailed description and related drawing figures.

BRIEF SUMMARY AND OBJECTIVES

The present disclosure describes an article and method for securing a catheter. The article may be used at operative sites, surgical sites, drain sites, port sites, catheter sites, wound sites, ostomy sites, or any other bodily location where drainage, or introduction of fluids, may occur or be performed.

The article is an assembly having parts: a conduit, a catheter, and a retainer; and may have other parts. The conduit has a medial bend and a lateral opening. The catheter is inserted into the conduit and is partially exposed by the lateral opening. The retainer enters the opening to secure the catheter by gripping its exposed portion.

An advantage of the present article is that it is able to be attached to an exterior surface of a body.

Another advantage is that it prevents accidental movement of the catheter.

Another advantage is that it prevents accidental removal or further insertion of the catheter relative to the body.

Another advantage is that it prevents constriction of the catheter.

Another advantage is that it provides a simplified use and especially a secure engagement of the catheter.

Another advantage is its ability to direct the catheter in any direction along and close to the exterior body surface to avoid entanglement with clothing and body movements.

The details of one or more embodiments of these concepts are set forth in the accompanying drawings and the description below. Other features, objects, and advantages of these concepts will be apparent from the description and drawings, and from the claims.

BRIEF DESCRIPTION OF THE SEVERAL VIEWS OF THE DRAWINGS

Like reference symbols in the various drawings indicate like elements.

DETAILED DESCRIPTION

Figure 1:
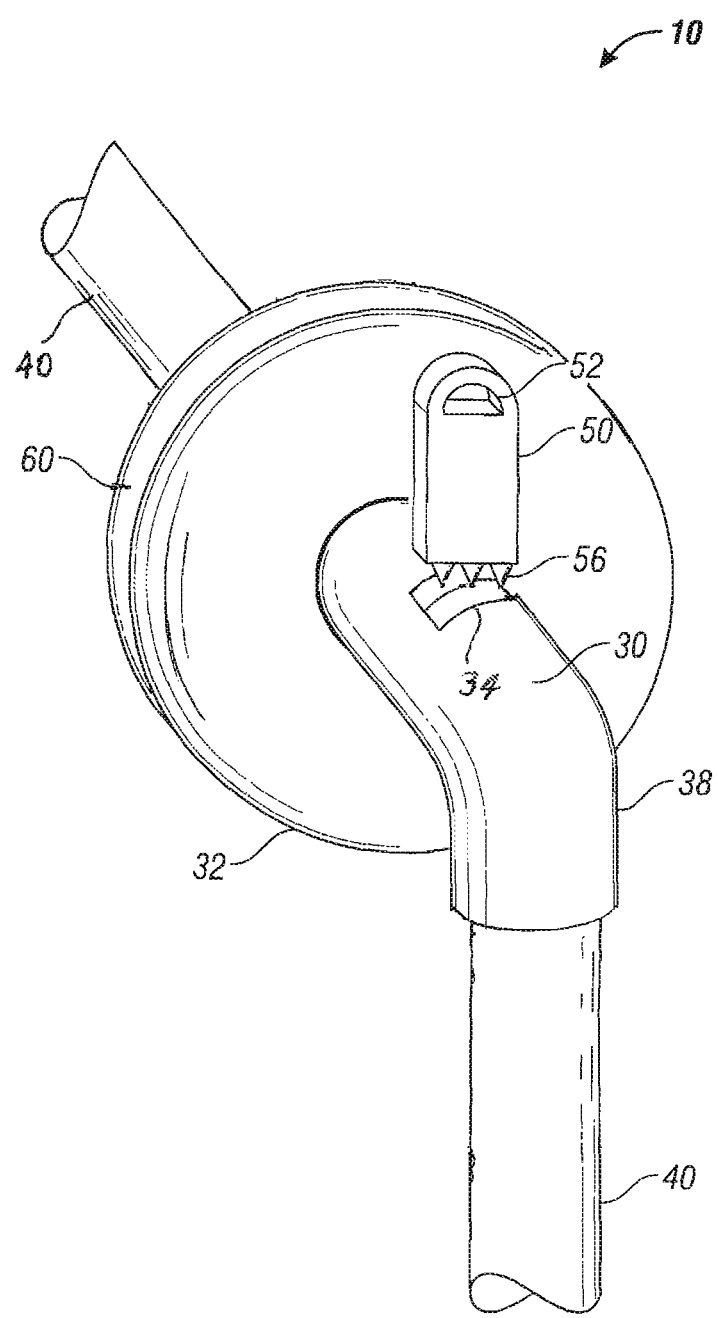
FIG. 1 is an example perspective view of the presently described article.

FIG. 1 shows a perspective view of an exemplary drainage device 10. As shown in FIG. 1, drainage device 10 includes a hollow conduit 30, a catheter 40, and a retainer 50. Conduit 30 has a base 32 at a proximal end of conduit 30, a lateral opening 34, and a medial bend 38. Catheter 40 is inserted into and through conduit 30 to an opposite end of conduit 30.

Figure 2:
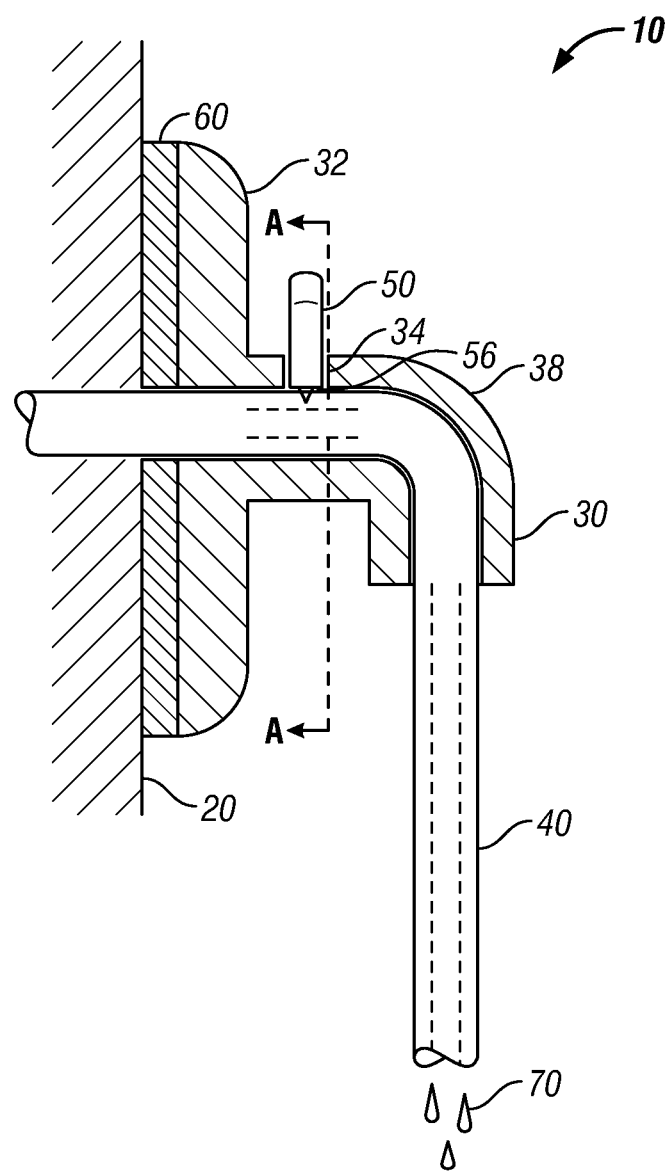
FIG. 2 is an example side sectional view of the article.

FIG. 2 is a side view of drainage device 10 showing a sectional view of conduit 30, but showing catheter 40 in full. In FIG. 2, retainer 50 is shown engaged with conduit 30. As shown in FIG. 2, drainage device 10 is attached to a body surface 20 (for example, an epidermis surface). Fluid(s) 70 may drain from catheter 40 at a distal end of conduit 30.

A method of using drainage device 10 includes inserting catheter 40 into conduit 30, adhering conduit 30 to body surface 20, and engaging retainer 50 with conduit 30 to secure catheter 40 in place. A method of use may also include disengaging retainer 50 from conduit 30 in order to remove catheter 40, e.g., for insertion of a replacement catheter.

Conduit 30 is generally formed of a rigid material in order to protect catheter 40. The material of conduit 30 has sufficient strength and/or hardness to prevent constriction of catheter 40. However, conduit 30 may be made formed of a somewhat flexible material, or a material which is rigid at normal temperatures, but becomes flexible upon heating (e.g., for adjusting an angle of medial bend 38, discussed below).

Conduit 30 may be normal to base 32, e.g., may extend perpendicularly from base 32. Base 32 has a surface which attaches to the body at a location where catheter 40 is to be inserted. Base 32 surrounds an opening in body surface 20 from which fluid(s) 70 are to be drained or introduced via catheter 40. The surface of base 32 may be adhesive for adhering to body surface 20.

However, as shown in FIGS. 1 and 2, drainage device 10 may also include a mounting patch 60 having an adhesive proximal side which adheres to body surface 20 and a distal side secured to conduit 30. Mounting patch 60 is generally co-extensive with base 32, e.g., in contact with an entire surface of base 32.

Medial bend 38 bends conduit 30 at an angle. Conduit 30 is bent at an angle of between 45 and 135 degrees. In a preferred embodiment, conduit 30 is bent at an angle of 90 degrees. Medial bend 38 is generally located midway between the ends of conduit 30, but may be located closer to one end of conduit 30. The angle of medial bend 38 may be very important medically. For example, in individual cases there may be a critical or ideal angle of medial bend 38 depending upon the particular use of catheter 40, the location on skin surface 20, or other factors.

Medial bend 38 helps prevent accidental movement or removal of catheter 40. For example, an unsheathed portion of catheter 40 extending from conduit 30 may be accidently bumped, pushed, pressed, or otherwise moved about. Medial bend 38 prevents this movement from being transmitted to an opposite end of catheter 40 located inside the body. In combination with the securing aspects of retainer 50, medial bend 38 provides even greater security in holding catheter 40 in place and preventing the accidental movement or removal of catheter 40.

Medial bend 38 may also allow the distal end of conduit 30 to be pointed in a general direction of gravitational flow of fluid(s) 70, to facilitate drainage of fluid(s) 70. Medial bend 38 also allows an exterior portion of catheter 40 to be directed along a surface of the body, rather than protruding obtrusively away from the body. Medial bend 38 may point the distal end of conduit 30 away from lateral opening 34.

Figure 3:
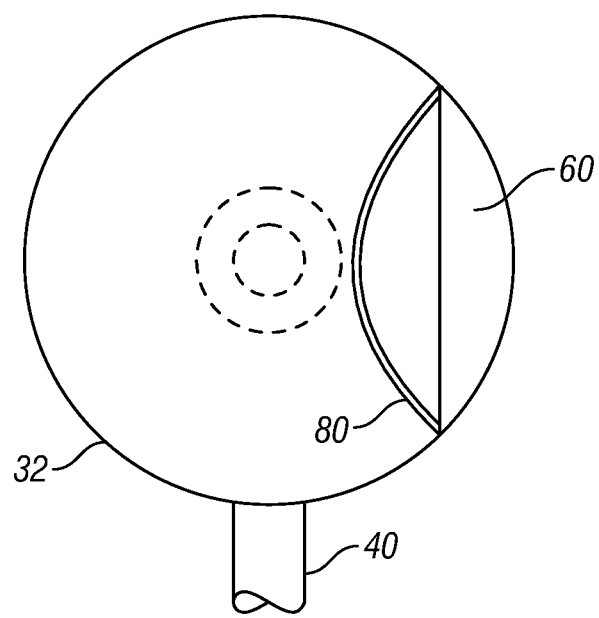
FIG. 3 is an example rear elevational view in an embodiment of the article.

FIG. 3 shows a rear view of drainage device 10. As shown in FIG. 3, an optional peel-away cover 80 may be in contact with a surface of base 32 or mounting patch 60. Cover 80 may have a non-adhesive proximal surface and may have a distal surface in contact with the adhesive proximal surface of mounting patch 60. Cover 80 may prevent drainage device 10 from undesirably adhering to surfaces prior to its use. Once drainage device 10 is ready for application to a body, cover 80 may be removed from drainage device 10, thereby exposing a surface of base 32 or mounting patch 60 for application to body surface 20.

As shown in FIG. 3, base 32 may have a circular shape. However, other shapes, such as square, rectangular, oval, etc. are possible. The surface of base 32 may be planar, convex, concave, or have another type of contour adapted for adhesion to various flat, curved, or irregular surfaces of the body to which conduit 30 is to be attached.

Figure 4:
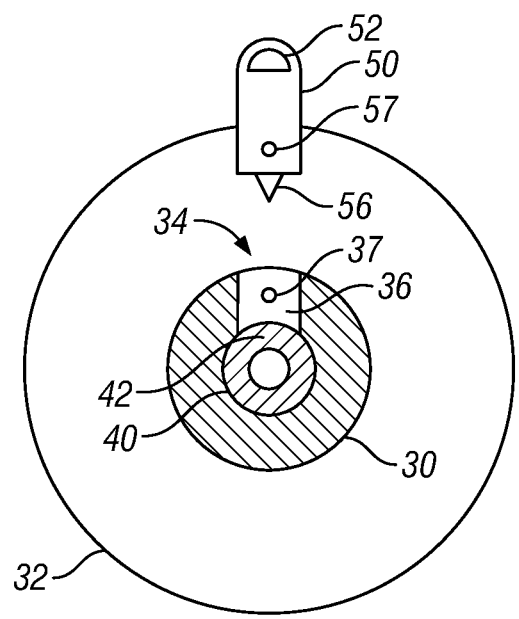
FIG. 4 is an example front sectional view along cutting plane line A-A of FIG. 2.
Figure 5:
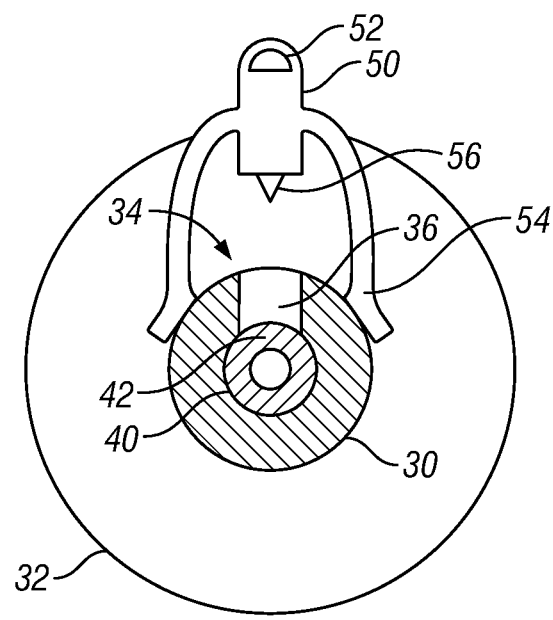
FIG. 5 is an example front sectional view along cutting plane line A-A of FIG. 2 in a further embodiment of the article.
Figure 6:
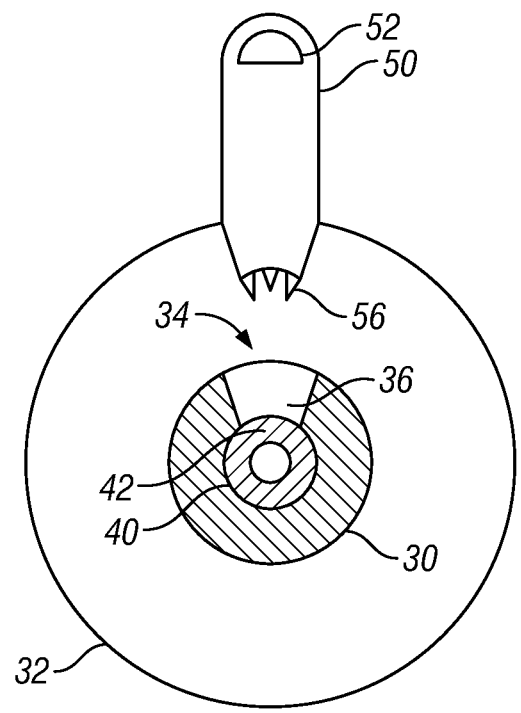
FIG. 6 is an example front sectional view along cutting plane line A-A of FIG. 2 in a still further embodiment of the article.

FIGS. 4-6 show front sectional views of various embodiments of drainage device 10. As shown in FIGS. 4-6, retainer 50 may have a finger hold 52 for facilitating engagement and removal of retainer 50. Finger hold 52 may be a hole extending through retainer 50, or may be a depression in, or protrusion from, one or more sides of retainer 50. Finger hold 52 allows retainer 50 to be held between a thumb and finger for easier engagement and disengagement with conduit 30.

As shown in FIGS. 4-6, conduit 30 may have an interior width the same as, or slightly wider than, a width of catheter 40. Thus, when catheter 40 is within conduit 30, catheter 40 is coaxial with conduit 30. In one example, catheter 40 has a width of 3 mm ("9 French" on the French catheter scale), catheter wall 42 has a width of 1 mm, and an interior width of catheter 40, e.g., a width of the hollow space within catheter 40, is 1 mm. Catheter 40 is generally made of a flexible, but durable material, e.g., plastic, such as polyurethane.

Lateral opening 34 of conduit 30 is an opening in a wall of conduit 30 which exposes an interior space 36. Lateral opening 34 may be located at a proximal side of conduit 30, for example, near base 32. When catheter 40 is within conduit 30, lateral opening 34 exposes a portion of catheter 40. Retainer 50 is engaged with conduit 30 at lateral opening 34.

Retainer 50 may be secured in a selected position relative to lateral opening 34 by various means to prevent accidental disengagement of retainer 50 due to bumping, pressure, or other forces upon retainer 50. A wall of conduit 30 at lateral opening 34 may have a surface which is complementary to a surface of retainer 50, enabling retainer 50 to fit securely in place within lateral opening 34. Alternatively or additionally, retainer 50 may be secured within lateral opening 34 by other means, such as legs, friction, and/or convergent surfaces, as described below.

Retainer 50 is generally made of a rigid material, but may also be made of a material providing some flexibility (e.g., plastic). Retainer 50 is removable from conduit 30 and is generally capable of being repeatedly engaged with and disengaged from conduit 30.

Retainer 50 contains at least one tooth 56 for securing catheter 40 within conduit 30 when retainer 50 is engaged with conduit 30. In some embodiments, plural teeth 56 are arcuately positioned (see, for example, FIG. 6). Tooth 56 is generally positioned to penetrate an outer surface of catheter wall 42 in order to secure catheter 40 within conduit 30. Alternatively, tooth 56 may not penetrate the outer surface of catheter wall 42, but simply deform the outer surface of catheter wall 42 and thereby achieve a similar result.

Preferably, tooth 56 does not penetrate through an entire width of catheter wall 42 into an interior of catheter 40. Penetration through catheter wall 42 to an interior of catheter 40 may cause undesirable leakage of fluid(s) 70.

As shown in FIG. 4, in one embodiment, retainer 50 is secured within lateral opening 34 by complementary surfaces. FIG. 4 shows a wall of conduit 30 has a surface feature 37, and retainer 50 has a corresponding surface feature 57. Surface feature 37 may be a convex protrusion, and corresponding surface feature 57 may be a concave indentation which receives the convex protrusion. Alternatively, surface feature 37 may have a concave shape and corresponding surface feature 57 may have a convex shape.

The complementary surfaces may be shaped such that they "snap" or "lock" into each other by the application of force (e.g., by pushing retainer 50 into lateral opening 34), and "unsnap" or "unlock" from each other by the application of force in an opposite direction (e.g., by pulling retainer 50 away from lateral opening 34).

As shown in FIG. 5, in one embodiment, retainer 50 includes legs 54 at opposite sides of retainer 50. FIG. 5 shows legs 54 extending from retainer 50, giving retainer 50 a U-shape. When retainer 50 is engaged with conduit 30, legs 54 surround conduit 30 and/or grip sides of conduit 30. Legs 54 may be spring-like in order to allow a distance between legs 54 to expand in order to accommodate a width of conduit 30 when engaging and disengaging retainer 50 with conduit 30 (e.g., "clipping" and "unclipping" retainer 50 onto/from conduit 30). Legs 54 extend to an opposite side of conduit 30 from lateral opening 34, and thus prevent accidental disengagement of retainer 50 by inadvertent bumping, pressure, or force placed upon retainer 50.

As shown in FIG. 6, in one embodiment, conduit 30 and retainer 50 have converging sidewalls. Retainer 50 may be held in place by friction between the sidewalls of conduit 30 and sidewalls of retainer 50 retainer 50. Other means of securing retainer 50 within lateral opening 34 are possible.

However, in any embodiment, retainer 50 is generally able to be repeatedly engaged and disengaged from conduit 30, but, while engaged with conduit 30, able to securely hold catheter 40 despite minor bumping, pressure, or other forces upon retainer 50.

In a method of securing and directing a catheter, hollow conduit 30 is formed, having medial bend 38 at an angle of between 45 and 135 degrees. Lateral opening 34 is formed in the wall of conduit 30. Catheter 40 is engaged coaxially within conduit 30. Retainer 50 is removably engaged within the lateral opening 34, thereby penetrating catheter wall 42 by a tooth 56 of the retainer 50. A terminal end of the conduit 30 is positioned, thereby directing an exterior portion of the conduit 40 selectively. Finally, conduit 30 is affixed to body surface 20, thereby securing the direction of the external portion of conduit 40 semi-permanently.

Embodiments of the subject apparatus and method have been described herein. Nevertheless, it will be understood that various modifications may be made without departing from the spirit and understanding of this disclosure. Accordingly, other embodiments and approaches are within the scope of the following claims.

What is claimed is:

1. A drainage device comprising:
   a hollow conduit having a medial acute angular bend, and further having a lateral opening limited to a medial position in a wall of the hollow conduit proximal to the medial acute angular bend, the lateral opening exposing an interior space within the hollow conduit, the wall having a means for securing a retainer in a selected position within the lateral opening;
   a catheter positioned coaxially within the hollow conduit, the catheter having a catheter wall; and
   with the retainer secured in the selected position a tooth of the penetrates the catheter wall, the retainer and the conduit wall having mutually mating circular convex and circular concave surface features extensive from planar surfaces.

2. The drainage device of claim 1, wherein the retainer has opposing finger depressions therein.

3. The article of claim 1, wherein the retainer has plural teeth arcuately positioned.

4. The article of claim 1, wherein the retainer has a through hole in a position for gripping the retainer when the retainer is engaged with the conduit wall.

5. The article of claim 1, wherein the retainer has plural teeth directed toward the catheter when the retainer is positioned within the lateral opening.

6. The article of claim 5, wherein the plural teeth are arranged arcuately.

7. The article of claim 1, wherein the hollow conduit is formed integrally with a base and extends from the base.

8. The article of claim 7, wherein the lateral opening is adjacent to the base.

9. A method for securing and directing a catheter of a drainage device relative to an epidermis surface, the method comprising:
   forming a hollow conduit with an acute medial bend therein;
   forming a lateral opening in a wall of the hollow conduit, the lateral opening limited to a medial position of the hollow conduit proximal to the acute medial bend;
   positioning the catheter coaxially within the hollow conduit;
   engaging a retainer within the lateral opening in a position whereby a tooth of the retainer penetrates a wall of the catheter, the retainer and the hollow conduit wall mutually mating at circular convex and circular concave surface features extending from planar surfaces; and
   affixing a terminal end of the catheter to the epidermis surface.

10. The method of claim 9, further comprising forming a through hole in the retainer in a position for gripping the retainer when the retainer is engaged with the lateral opening.

11. The method of claim 9, further comprising forming plural teeth on the retainer, and directing the teeth toward the catheter when the retainer is being positioned within the lateral opening.

12. The method of claim 11, further comprising arranging the plural teeth arcuately.

13. The method of claim 9, further comprising forming the hollow conduit integrally with a base and extending the hollow conduit from the base.

14. The method of claim 13, further comprising positioning the lateral opening adjacent to the base.

* * * * *